United States Patent [19]

Corrigan et al.

[11] Patent Number: 4,533,648
[45] Date of Patent: Aug. 6, 1985

[54] REGENERATION OF COPPER CHROMITE HYDROGENATION CATALYST

[75] Inventors: Patrick J. Corrigan, Fairfield; Richard M. King; Scott A. VanDiest, both of Cincinnati, all of Ohio

[73] Assignee: The Procter & Gamble Company, Cincinnati, Ohio

[21] Appl. No.: 602,887

[22] Filed: Apr. 23, 1984

[51] Int. Cl.³ .................. B01J 23/94; B01J 23/92; C07C 34/20; C07C 29/136
[52] U.S. Cl. ........................ 502/38; 502/41; 568/864; 568/885
[58] Field of Search ............ 502/20, 34, 38, 41, 502/56; 568/864, 885

[56] References Cited

U.S. PATENT DOCUMENTS

| | | | |
|---|---|---|---|
| 1,022,347 | 4/1912 | Wilbuschewitsch | 502/24 |
| 2,235,702 | 3/1941 | Endres | 518/885 |
| 3,346,484 | 10/1967 | Lewis | 502/34 |
| 3,699,054 | 10/1972 | Organ et al. | 502/33 |

Primary Examiner—P. E. Konopka
Attorney, Agent, or Firm—Richard C. Witte; Ronald L. Hemingway

[57] ABSTRACT

Spent copper "chromite" catalyst from the hydrogenation of carboxylic acids or esters of such acids is regenerated by vacuum treatment at high temperature to reduce the level of organic residue on the catalyst to less than about 25%, followed by oxidation.

14 Claims, 2 Drawing Figures

REGENERATION OF COPPER CHROMITE HYDROGENATION CATALYST

FIELD OF THE INVENTION

This invention pertains to the field of hydrogenation of carboxylic acids and esters of said acids and, in particular, to the regeneration of the copper chromite catalyst used to facilitate the hydrogenation reaction.

BACKGROUND OF THE INVENTION

This invention relates to the field of hydrogenation of carboxylic acids containing six or more carbon atoms and esters of such acids to form the corresponding alcohols, (i.e. alcohols which contain six or more carbon atoms). Such alcohols are valuable intermediates in the production of synthetic detergents, polymers and lubricants. More particularly, the invention relates to the regeneration of spent catalyst of the type commonly referred to as "copper chromite," when said catalyst has lost its activity in the course of being employed in the hydrogenation process.

So-called copper chromite, which is usually a mixture of cupric oxide and cupric chromite, is widely employed as a hydrogenation catalyst. Many hydrogenation process variations are employed, but one commmon embodiment comprises suspending finely-divided copper chromite in a liquid reaction mix comprising the acid, ester, alcohol or mixtures thereof, while hydrogen is passed through the suspension under conditions of elevated temperature and pressure. The copper chromite is then removed from the hydrogenation product by any suitable means, such as filtration or centrifugation, and returned to the reaction step for reuse. In the course of the hydrogenation reaction, at a rate which is dependent upon many factors including the nature of the reaction mix and the stringency of the reaction conditions being employed, a portion of the copper chromite catalyst is deactivated, with the result that it is necessary, either continuously or intermittently, to withdraw the deactivated material and replace it with fresh copper chromite.

Ordinarily the spent catalyst is either discarded or sold at a fraction of its original cost for recovery of its metal values. This results in a substantial cost to the hydrogenation process, and there has long been a recognized need for a practical method of restoring the spent catalyst to its active condition.

U.S. Pat. No. 3,699,054, Organ et al., issued Oct. 17, 1972, incorporated by reference herein, discloses a process for regenerating copper chromite catalyst, comprising the steps of:
(a) washing the catalyst in a volatile solvent (e.g., methanol) to remove organic residues from the hydrogenation reaction;
(b) drying the washed catalyst to free it of the residual solvent; and
(c) heating the dried catalyst in an atmosphere containing oxygen (e.g., in air) at a temperature of 100° C. to 500° C. for at least about 15 minutes.

This process, when practiced on a commercial scale, suffers from the practical disadvantage of the need for handling and recovering large quantities of volatile solvents.

It is the principal object of the present invention to provide a process for regenerating the copper chromite catalyst used in hydrogenation process, without the need to use solvents.

SUMMARY OF THE INVENTION

In accordance with the present invention, spent copper chromite catalyst containing organic residue from the hydrogenation process in which it has been used, is reactivated by subjecting it to the following process:
(1) the spent catalyst is subjected to a vacuum of 1 to 20 mm Hg at a temperature of 65° C. to 320° C. for a period of time sufficient to reduce the organic residue content of the spent catalyst to less than about 25% by weight;
(2) the vacuum-treated catalyst from Step (1) is heated in an atmosphere comprising molecular oxygen, at a temperature of from about 260° C. to 370° C., whereby the remaining organic residue is burned off and the catalyst is reoxidized.

The oxidized catalyst, after cooling, is suitable for reuse as a catalyst in the hydrogenation process.

DESCRIPTION OF THE PREFERRED EMBODIMENTS

Figure 1:
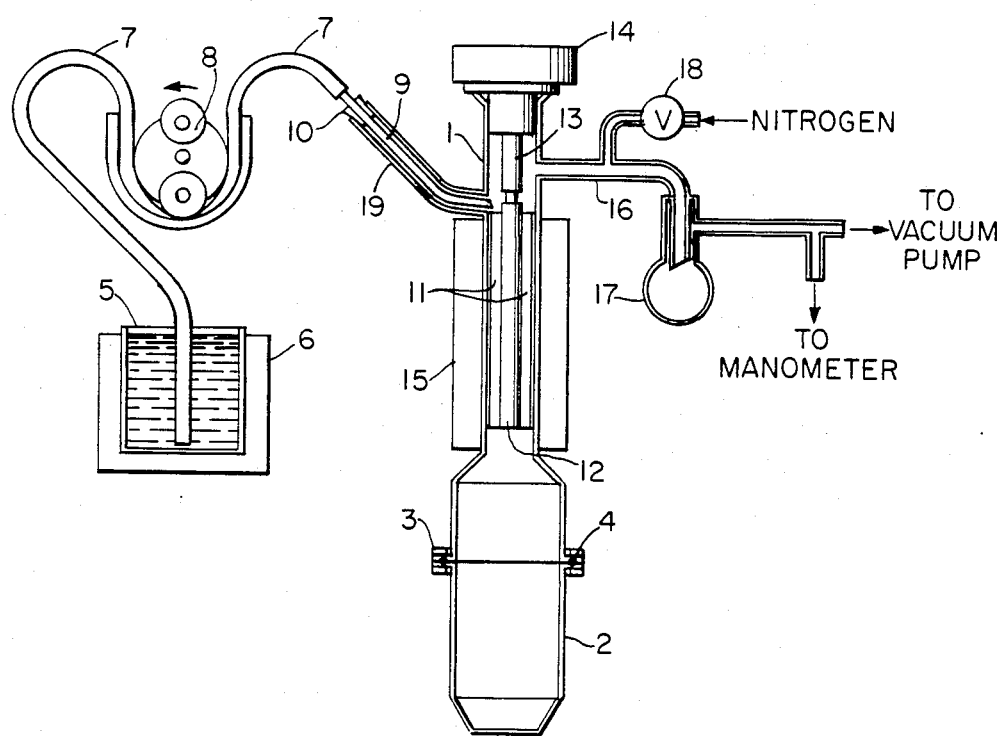
FIG. 1 is a front elevational view of a vacuum thin film dryer apparatus used in Example I, herein.

The catalyst which is the subject of the regeneration of this invention is that material which is known as "copper chromite." It will be recognized that this material is, ordinarily, actually an intimate mixture which consists essentially of cupric oxide and cupric chromite. The catalyst may also contain lesser amounts of various stabilizers such as barium oxide and manganese oxide. The catalyst will typically be in a more or less finely subdivided form, e.g., about 1 to 100 microns, but it may also, if desired, be employed as particles of larger size. Inasmuch as the catalytic activity, the deactivation phenomena, and reactivation process as described herein are all basically surface phenomena, the applicability of the invention is not controlled by catalyst particle size.

The organic material which is present in admixture with the spent catalyst prior to regeneration is the residue from the hydrogenation process. It comprises primarily alcohol products from the hydrogenation process, but may also include minor amounts of various organic by-products and intermediates.

The hydrogenation reaction in which the copper chromite catalyst is used is the reduction of carboxylic acids containing at least six carbon atoms, or esters of said acids, to the corresponding alcohols; for example, the reduction of lauric acid to lauryl alcohol or the reduction of methyl laurate to lauryl alcohol and methanol. The carboxylic acids have the formula RCOOH, wherein R is an alkyl or alkenyl chain having from about 5 to about 29, preferably from about 7 to about 21, and most preferably from about 7 to about 17, carbon atoms. In the case of esters of these acids, the alcohol moiety of the ester will be an alcohol containing from about 1 to about 30, preferably from about 1 to abut 4 carbon atoms. Normally the acids will have a total carbon atom content of from about 6 to about 30, preferably about 8 to about 18. Normally, the esters will have a total carbon atom content of from about 7 to about 31, preferably about 9 to about 19 carbon atoms.

The acids herein can be mono-, or dicarboxylic. The acid moiety of the esters can be mono-, or dicarboxylic and the alcohol moiety of the ester can contain from 1 to 3 hydroxy groups. Examples of carboxylic acids used in the hydrogenation process are caproic, capric, lauric, palmitic, stearic, lignoceric, adipic, and sebacic. Examples of esters are methyl caproate, ethyl caprate, methyl laurate, propyl laurate, butyl palmitate, methyl oleate, ethyl stearate, methyl lignocerate, lauryl propionate, stearyl butyrate, lauryl caprate, mono- or dimethyl ester of adipic acid, mono- or di-hexanediol ester of adipic acid, mono- or di-methyl ester of sebacic acid, mono-, di, or tri-glycerides such as glycerol monolaurate, glycerol distearate, trilaurin, oleolauromyristin, tristearin, and triolein.

If the acid or ester is unsaturated, any double bonds will be completely hydrogenated in addition to the conversion of the acids or esters to alcohols.

The acids of primary interest are the $C_6$ to $C_{22}$ fatty acids. The esters of primary interest are the methyl esters of $C_6$ to $C_{22}$ fatty acids and the adipic acid diester of 1,6-hexanediol.

Typically, the catalyst is removed from the product of the hydrogenation reaction by filtering or centrifugation. The separated spent catalyst will normally comprise from about 25% to 50% spent catalyst and 50% to 75% organic matter, and is in the form of a pasty solid or slurry.

All percentages and proportions set forth herein are "by weight" unless specified otherwise.

In the first step of the process of the invention, the content of the organic matter in the spent catalyst is reduced to a point where the catalyst is a free-flowing powder, suitable for subsequent treatment in a reactor where the catalyst will be contacted with oxygen, such as a fluidized bed reactor. In order to obtain a free flowing powder, the level of organic material in the catalyst must be reduced to about 25% or less, preferably less than 20% and most preferably less than 10%. At levels of organic material above about 25%, the surface of the catalyst is completely covered with organic matter, shielding the catalytically active sites from contact with oxygen. Since the second (oxygenation) step of this regeneration process involves the burning off of the residual organic material, especially that within the pores of the catalyst, and since this burning process is essentially the catalytic combustion of the organic material, the shielding of the catalytic sites by the organic material significantly inhibits the process. Until enough organic material is stripped away to expose the catalyst surface to molecular oxygen, the burning process will be slow since the temperatures involved (260°–370° C.) are much below the autoignition temperatures for the organic material. Once the burning process begins, high levels of organic material on the catalyst will result in a higher heat release during combustion, complicating the heat removal problem. The transfer of heat away from the catalyst during combustion must be very efficient and very carefully controlled since temperature excursions above about 425° C. will permanently deactivate the catalyst. A further complication of high organic levels on the catalyst is that above about 25% organic material, the catalyst mixture tends to be waxy or sticky, and this tendency becomes very pronounced above about 30%. Catalyst in this state is difficult to handle, being granular or globular in consistency or even paste-like or sludge-like, depending on the nature and level of organic material on the catalyst. This type of material is difficult to transfer between process steps and may not even be suitable for use in reactors (such as fluidized beds) which are suitable for carrying out the second (oxygenation) step of the process herein.

In order to accomplish the reduction of organic material, the catalyst-fatty alcohol product from filtration or centrifugation is subjected to a subatmospheric pressure of from about 1 to 20 mm (preferably 1 mm to 10 mm) Hg and a temperature high enough to evaporate the highest boiling alcohol product recovered with the catalyst from the hydrogenation reaction. This temperature for a given alcohol or mixture of alcohols can be determined from any convenient source of vapor pressure versus temperature information for fatty alcohols, such as a Cox chart. The specific temperature required to reduce the organic content of the catalyst to less than 25% will vary, depending on the specific vacuum applied and the specific alcohol or mixture of alcohols, but will generally be in the range from about 65° C. to about 320° for vacuums of 1 to 20 mm and for $C_6$ to $C_{30}$ fatty alcohols. If high boiling acids or esters (e.g., stearic acid or methyl esters of tallow fatty acids) were used to form the alcohols, then a temperature from the higher portion of the temperature range will be required. If the alcohols were formed from the hydrogenation of lower boiling acids or esters, then correspondingly lower temperatures will be used.

The apparatus and the temperature/pressure conditions used for vacuum treatment of spent catalyst should provide for a very short residence time, i.e., the organic matter should be very rapidly evaporated from the catalyst. The reason for this is that when alcohols, particularly those containing more than about 6 carbon atoms, are contacted with copper chromite under even mild conditions of heat and vacuum, dehydrogenation of the alcohol functional group occurs. This dehydrogenation of the alcohol forms the corresponding aldehyde, and molecular hydrogen. The aldehyde will react further with alcohols to form long chain, high boiling compounds such as acetals and hemiacetals. These high boiling compounds are difficult to remove from the catalyst, even under extreme conditions of heat and vacuum. Since a noticeable buildup of aldehydes and high boiling compounds will occur after only a few minutes of application of heat and vacuum, it is desirable to have the residence time of the spent catalyst in the vacuum apparatus be as short as practicable. Generally, the residence time of the spent catalyst in the vacuum/heat treatment of Step (1) of the process herein should be less than about one minute, preferably less than about 30 seconds.

The type of apparatus used for the spent catalyst must be one that will convert the spent catalyst to a free-flowing granular state with a minimum time of exposure to heat and vacuum. This apparatus should be one which is efficient in rapidly exposing the surfaces of the catalyst particles to both the heat transfer medium and the low pressure within the apparatus. A preferred type of apparatus is a vertical thin-film dryer, such as that manufactured and sold by Luwa Corporation, CP Type.

The catalyst, once the bulk of the organic material has been removed, is pyrophoric when exposed to oxygen. This is because the cupric oxide on the surface of the cupric chromite has been reduced in the hydrogenation reaction to finely divided copper metal ($Cu°$). Under conditions where the catalyst is slurried in carboxylic acids, alcohols or esters, or in any other way covered with organic material above the level of about 25% by weight, the surface copper is shielded from any oxygen present around it by the organic material covering the surface of the catalyst. However once the organic material has been removed, the reduced surface copper becomes exposed, and it will react with any available oxygen. If the level of oxygen is high enough, such as that present in air, the reduced copper will react very rapidly with the oxygen to form cuprous oxide ($Cu^{+1}$). Since this is an exothermic reaction, some heat is generated within the catalyst. At temperatures above about 10°–20° C., the oxidation of copper to cuprous oxide is rapid enough to cause the temperature of the catalyst to rise significantly, and if the temperature rises to about 90° C., catalytic combustion of the organic material by oxygen and the copper chromite catalyst occurs. Once this combustion has started, it can become uncontrolled. The temperature rises rapidly, and may reach as high as 650° C. Large amounts of noxious smoke and flames are associated with this combustion. The smoke indicates incomplete combustion of the organic material, containing vaporized alcohols and aldehydes, carbon dioxide, water vapor and numerous catalytically altered hydrocarbon products. As a result of this uncontrolled oxidation, the catalyst will generally turn grey, and will be permanently catalytically inactive.

In order to avoid combustion problems during the transfer of the pyrophoric catalyst between the process steps of removing the organic material and combusting the organic material in a controlled manner, the catalyst must be either kept out of contact with oxygen completely, or allowed to come into contact with oxygen in a manner so that the reduced copper is oxidized without a heatup that will ignite the organic material on the catalyst. To keep the catalyst out of contact with oxygen, the catalyst can be transferred between process steps under vacuum (preferably at less than about 100 mm Hg), or under a blanket of an inert gas such as nitrogen or carbon dioxide. If it is desired to handle the dried catalyst in air it is necessary to carefully oxidize the surface copper prior to handling in air. Oxidation of the surface copper, can be accomplished by very slowly bleeding in an oxygen containing gas, such as air, at a temperature up to about 10° C. while simultaneously agitating the catalyst, so that any heat generated is quickly dissipated so as to avoid combustion of any residual organic material. Depending on the quantity of catalyst involved, this procedure may require several minutes to several hours to complete. The lower the temperature, the faster the rate at which oxygen can be bled in. Preferably the oxygen is bled into the catalyst at a temperature below about 10° C. This is conveniently accomplished by keeping the vessel containing the catalyst immersed in an ice water bath. Exposing the catalyst to oxygen at a rate which avoids buildup of heat, oxidizes only the surface of the catalyst copper to $Cu^{-1}$, and has no effect on the organic matter associated with the catalyst.

After the removal of the bulk of the organic matter from the spent catalyst in Step (1) of the process herein and after the catalyst has been transferred to the combusting apparatus, the granular catalyst powder is contacted with a gas containing molecular oxygen, at an elevated temperature, while being agitated, so as to prevent the formation of zones of localized overheating. Since this reaction is highly exothermic, this step must be conducted in an apparatus with extremely good heat transfer capabilities. The preferred type of apparatus for this step is a fluidized bed.

The gas contacted with the catalyst must contain enough molecular oxygen to completely combust all of the remaining organic material on the catalyst. Generally any level of oxygen from about 1% to 100% in the gas may be used. The bulk of the gas besides the oxygen should be an inert gas, such as carbon dioxide, nitrogen, argon, or helium. Reactive gases such as chlorine or flourine, or compounds of sulfur or phosphorous must be avoided since even trace amounts of these compounds will result in a permanent loss of catalyst activity. Compounds of nitrogen other than molecular nitrogen, compounds of carbon other than carbon dioxide, or compounds containing boron, bromine, iodine, hydrogen, or metals should also be avoided.

The higher the levels of oxygen in the combusting gas, the more care that must be taken to control temperature excursions within the catalyst mixture. The catalyst should not be exposed to temperatures higher than about 425° C., even for short periods of time, since this will result in the degradation of the catalyst, and permanent loss of activity. Care must be taken that the temperature in the apparatus is at least about 260° C., in order to insure that complete combustion occurs, especially if the combusting gas contains a low level (i.e. less than about 10%) oxygen. In general treating the catalyst with oxygen at temperatures lower than 260° C. may result in organic residues remaining on the surface of the catalyst, and therefore incomplete regeneration of catalyst activity. Preferably, the temperature range should be between 315°–370° C.

Various techniques may be used in contacting the catalyst with the gas in order to properly combust the organic material without ruining the catalyst. A gas with low levels of oxygen may be preheated to a suitable temperature so that the combined effects of the hot gas and the organic combustion keep the catalyst temperature between 260°–370° C. Alternately, a gas with a suitable mixture of oxygen and an inert gas, may be passed through the catalyst at such a rate that the bulk of the heat of combustion is removed by the gas itself, while only a portion of the oxygen actually reacts with the organic material. Another method that may be used in controlling temperature is to alternate the passing of oxygen-containing gas and inert gas over the catalyst. The oxygen-containing gas is applied until combustion begins, then the pure inert gas is applied until the temperature excursion ceases, and then the oxygen-containing gas is applied again. This procedure is continued until the application of oxygen-containing gas at temperatures above about 260° C. no longer results in any temperature change. This indicates that no more organic material is on the catalyst.

In general, the oxidation of the organic material on the catalyst is very rapid at temperatures above about 260° C. In any apparatus where the amount of oxygen present is greater than the stoichiometric amount for the complete combustion of all the organic material present on the surface of the catalyst, and the temperature is above 260° C., the complete combustion will occur within several seconds.

In order to control this combustion and prevent undesired temperature excursions it is best to conduct the reaction using a dominant bath approach. Thus, in a continuous reactor, such as a backmixed reactor, or more specifically a fluidized bed reactor where the bulk of the material will be previously regenerated catalyst, only the catalyst entering the reactor will be combusting and releasing heat. The regenerated catalyst already in the reactor will act as a heat sink thereby assisting in control of the reaction.

In the process of oxidizing the organic material on the surface of the catalyst, a small portion of the oxygen present will react to oxidize the surface copper on the catalyst to cupric oxide, this copper having been reduced under the process of hydrogenation to copper metal (Cu°). This oxidation of copper to cupric oxide consumes a relatively small amount of oxygen and generates a relatively small amount of heat compared to the oxidation of the organic material.

The catalyst, as it emerges from the controlled combustion step is not pyrophoric. The surface copper has been oxidized to cupric oxide ($Cu^{+2}$), and there is substantially no organic matter left on the catalyst. This catalyst has the physical and chemical properties of copper chromite catalyst that has never been subjected to the conditions of hydrogenation.

After completion of the oxidation step just described, the oxidized catalyst is cooled, and is then ready for reuse as a hydrogenation catalyst.

The following examples are given to illustrate the invention further. It will be understood that these examples are given by way of illustration and that, within the scope of the invention, many variations can be made.

EXAMPLE I

Figure 2:
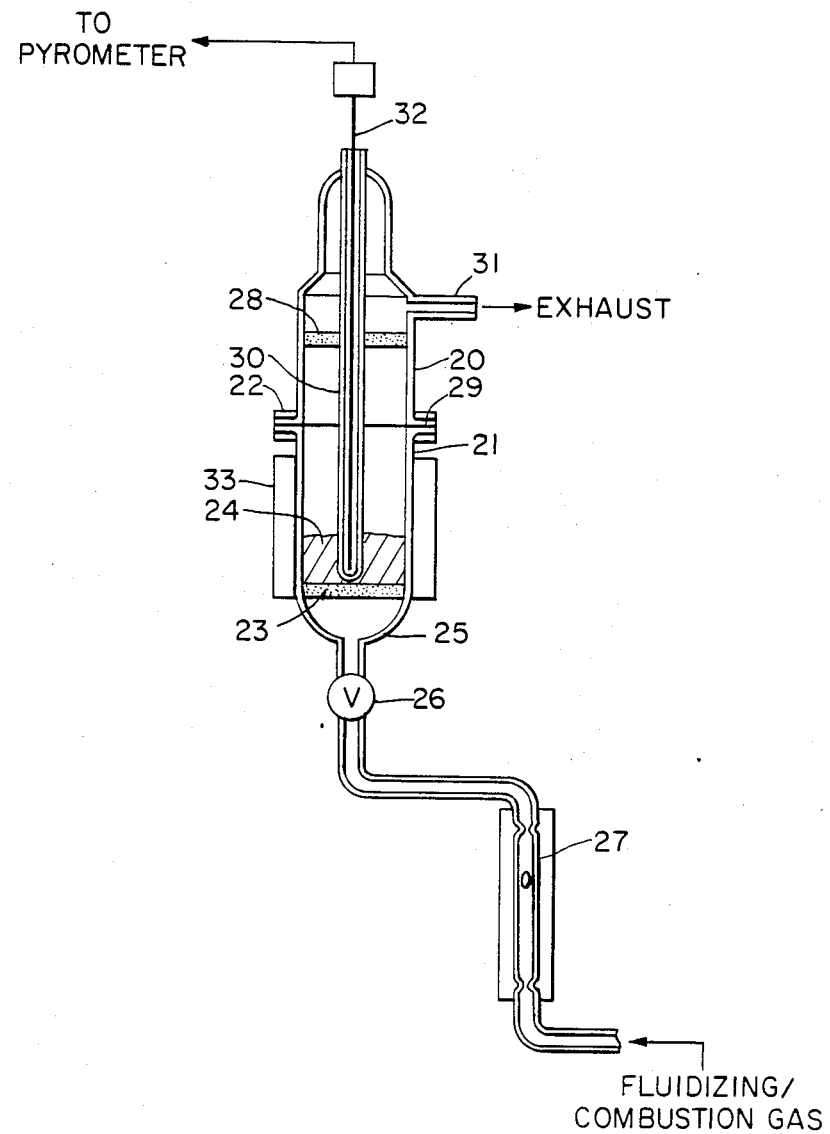
FIG. 2 is a front elevational view of a fluidized bed apparatus used in Example I, herein.

FIGS. 1 and 2 are front elevational views of apparatus which are employed in this example. The apparatus shown in FIG. 1 is a glassware thin film dryer, constructed by modifying a wiped film evaporator (Pope Scientific) to handle solids. A 2 inch (5.1 cm) diameter glass body 1, flared at the bottom, connects at the bottom to a 1-liter resin flask 2. The resin flask serves as a solids receiver, and the vacuum seal between the flask and body is accomplished by means of a clamp 3 and O-ring 4. There are two arms at the top of the glass body, one 19 for the introduction of slurry feed, and the other 16 for drawing off distillate.

Spent catalyst slurry (10–50% catalyst by weight) is kept warm (38°–50° C.) in a 500 ml. beaker 5 surrounded by an electric heating mantle 6. The slurry is drawn out of the beaker, through ⅛ inch (0.03 cm) I.D. Tygon tubing 7 by a peristaltic pump 8 at a rate of 1–2 g/min. The tubing at the discharge of the pump is connected to a 6 inch (15.2 cm) length of ⅛inch (0.3 cm) glass tubing 9, bent in an "L" shape to conform to the shape of the feed arm 19. The glass tube is inserted through a #5 rubber stopper 10 which maintains the seal at the feed arm. The feed slurry drips from the end of the glass tube down into the body 1, where it is wiped against the wall into a thin film by 3 rotating graphite blades 11. The blades are equally spaced, and held in position by a wiper retainer 12, which in turn is connected to a drive shaft 13. The drive shaft is rotated by an electric drive motor 14. The walls of the glass body are kept hot by a heating mantle 15, and the external wall temperature is maintained precisely by means of a thermostat and heating mantle controller (not shown). The wall temperature should be maintained at least 60° C. above the boiling point for the highest boiling organic component in the spent catalyst feed, for the particular vacuum in the dryer. When the spent catalyst has been used in the hydrogenation of methyl esters of coconut oil fatty acids, the temperature should be at least 200° C. at a vacuum of from about 3–5 mm Hg.

When the slurry is wiped in a thin film against the hot wall, the bulk of organic material on the surface of the catalyst flashes off, leaving the dry granular catalyst, containing about 10–20% of organic material. The granular catalyst (with the remaining organic matter trapped in the pores) falls into the catalyst receiver 2. The distilled organic material is drawn into the distillate arm 16 and condenses in the receiver flask 17. Vacuum is maintained at 3–5 mm of mercury in the dryer by means of a vacuum pump (not shown). Pressure is measured at the distillate receiver using a manometer (not shown). The distillate will typically contain 0.5–1.0% (by weight) entrained catalyst.

The catalyst, after treatment in the dryer, is pyrophoric when exposed to air. This is due to the reduced copper on the surface of the catalyst which will rapidly oxidize in the presence of oxygen at temperatures greater than 10° C. In order to protect the catalyst for further use, and for safe and efficient handling of the catalyst, a procedure has been devised to slowly oxidize the reduced copper to $Cu^{+1}$. Once this has occurred, the catalyst is safe to handle in air. This procedure is described below.

Once the required amount of slurry feed has been processed through the dryer, the feed pump and heating mantle are turned off, and the mantle is removed from the glass body. The entire apparatus is allowed to cool, under vacuum, to approximately 25° C. The vacuum pump is then shut off, and the vacuum in the dryer is broken with nitrogen through a valve 18. An ice water bath is placed around the catalyst receiver 2; and the clamp 3 and O-ring 4 are removed. The receiver and bath are then removed from the body of the dryer. The catalyst in the receiver (top open to air) is gently stirred for 1 hour at 0° C. After this treatment, the catalyst is safe to handle in air.

A certain percentage (10–50%) of the alcohol in the distillate flask will have been converted to fatty aldehyde. This occurs due to the dehydrogenation of the alcohol under the conditions of heat and vacuum, and in the presence of catalyst. At the higher levels of aldehyde formation, the distillate may become solid below 100°–120° F. due to the formation of alcohol-aldehyde complexes (acetals). This alcohol-aldehyde mixture can be reconverted to all alcohol by hydrogenating the distillate at 2000–3000 psi (140–210 kg/sq.cm) hydrogen, and 250°–310° C. Under these process conditions, the aldehyde is completely rehydrogenated to alcohol. No conversion of alcohol or aldehyde to hydrocarbon has been noted in this process.

The dried and cooled granular catalyst (with 10–20% organics) is next regenerated in a small glass fluidized bed shown in FIG. 2. The vessel is composed of two halves (20 and 21) which are held together at a ground-glass joint 29 by a clamp 22. At the bottom of the lower half is a porous glass frit 23, on top of which the catalyst sample 24 is placed. Below the glass frit is the plenum 25 where gas is introduced into the vessel. Gas is metered into the vessel by means of a metering valve 26 and flow meter 27.

The upper half of the vessel has a porous glass frit 28 situated about midway between the joint and the top of the vessel. Extending through the center of the frit 28, and through the top of the vessel, and sealed at both places, is a glass thermocouple well 30. The thermocouple well is of the proper length so that the bottom of the well will be 1 to 2 mm above the bottom frit 23 when the two halves of the vessel are sealed together.

This allows the well to extend 1–2 cm into the center of the catalyst sample. Just above the upper frit 28 is an exhaust port 31 for the exhaust of fluidizing and combustion gases.

Approximately 5 g of the dried catalyst from the thin film dryer are placed in the lower half of the vessel. The two halves of the vessel are connected and held in place with a clamp. A thermocouple 32 is placed in the thermocouple well, and is connected to a pyrometer for monitoring the temperature of the sample. A heating mantle 33 is placed around the outside of the glass vessel. A controller is connected to the pyrometer (not shown) and the heating mantle 33, and is set at 315° C. As the vessel heats up, a low flow (50–60 cc/min) of 10% $O_2$ in argon is blown through the plenum. When the temperature rises above 200° F. (93° C.), combustion of the organic material begins, and the temperature rises rapidly. The $O_2$/Ar flow is shut off, and $N_2$ flow (50–60 cc/min) is started. When the temperature stops rising, the $N_2$ is shut off, and the $O_2$/Ar flow resumed. This alternating pattern of $O_2$/Ar, then $N_2$ is repeated until the temperature remains steady under $O_2$/Ar flow at 315° C. At this point all of the organic material has been burned off, and the heat is coming entirely from the heating mantle. Care must be taken that the temperature never exceeds 425° C., or the catalyst will be ruined. Combustion products ($CO_2$, $H_2O$) and fluidizing gas will flow through the upper glass frit and out the exhaust port. Catalyst fines carried up with the gas will be filtered out by the upper frit.

The catalyst at this point is regenerated. The surface copper oxidation state is $Cu^{+2}$ and there are substantially no organics present. Once the catalyst is cooled down it can be reused the same as fresh catalyst.

Catalyst activity is measured by the following method. 49.5 g of methyl laurate are added to a 100 cc glass autoclave liner along with 0.5 g of copper chromite catalyst. A glass cap with a thermocouple well is inserted into the top of the liner and this assembly is placed in steel autoclave bomb. The bomb is placed in a heated rocking autoclave, and the catalyst-methyl laurate slurry is hydrogenated at 2000 psi (140 kg/sq.cm) $H_2$ and 270° C. for 1 hour. Activity of the catalyst is measured as the percentage of methyl laurate converted to lauryl alcohol. This percentage is determined by gas chromatograph.

The activity of the "spent" catalyst on the feed to the thin film dryer is generally 30–33. The activity of the "regenerated" catalyst is 48–50. Fresh, unused catalyst is also 48–50.

EXAMPLE II

This example illustrates vacuum treatment of spent catalyst (from the hydrogenation of coconut fatty acid methyl esters) on a commercial scale.

A Luwa type CP-210/800/10 vertical thin film dryer is employed in this example to remove organic material from the copper chromite catalyst. The dryer has 0.5 $m^2$ of heat transfer surface and hinged vertical blades for distributing the catalyst-organic feed slurry as a thin film around the heat transfer shell. A 5 HP motor drives the rotor and blades at a constant speed of 1000 rpm. The dryer shell is surrounded by a jacket which is heated by a hot oil system to 250° C. At the bottom of the dryer shell is a half ball valve which can be used to isolate the dryer from the dry product receiver.

The feed system to the dryer consists of a 50 gallon feed holding tank, a 1.5 GPM (5.7 l/min.) centrifugal feed pump and a feed preheater. The catalyst-organic feed slurry is kept at 50° C. in the feed tank by a set of steam coils immersed in the tank. Feed is drawn from the bottom of the tank by the feed pump and passed through a steam heated shell-in-tube heat exchanger to preheat a feed to 100° C. A backpressure regulator at the feed inlet to the dryer maintains about 20 psi (1400 g/sq.cm.) back-pressure.

The dry product receiver consists of a 46 cm. diameter stainless steel vessel with a 3 cm flange and O-ring at the open end at the top. This flange and O-ring are fitted to seal against the bottom flange of the dryer shell. When a vacuum is drawn in the receiver, the flanges are held in place by clamps. When the vacuum is broken and the clamps are removed, the receiver drops down onto a wheeled cart for easy transport. The receiver is designed to hold a 5 gallon (19 liter) steel bucket for convenient periodic removal of the solids during operation of the dryer. Connected to the side of the receiver are two ports. One port is connected to a nitrogen line to allow breaking the vacuum in the receiver with nitrogen. The second port is connected to a high capacity vacuum pump to allow for drawing a vacuum in the receiver.

The main vacuum in the dryer is drawn by a 4-stage air ejector system, operated by 150 psi (10,550 g/sq.cm.) steam. The vacuum in the dryer is monitored using a McCleod gauge.

At the vapor outlet of the dryer shell is an entrainment separator which consists of a small vessel packed with wire mesh. The entrainment is drained to a separate receiver. After passing through the entrainment separator, the organic vapor is condensed in a shell-in-tube heat exchanger, heated with hot oil to 70° C. Any low boiling materials will pass beyond this condenser to a second shell-in-tube condenser cooled to 25° C. with water.

In this example, the feed slurry to the dryer consists of 25% copper chromite, 51% lauryl alcohol, 20% myristyl alcohol, 3% cetyl alcohol, and the remaining 1% various other long chain organic compounds.

The slurry is fed to the dryer at a rate of about 110 lb/hr (50 kg/hr). The dry product receiver will hold about 40 lbs (18 kg) of catalyst, and therefore must be emptied about once an hour. The dry product is removed by first shutting the ball valve at the bottom of the dryer shell, and then breaking the vacuum in the receiver with nitrogen. The clamps are loosened, the receiver is lowered onto the wheeled cart, the bucket inside removed, and an empty bucket placed inside. A tight fitting cap must be placed on the full bucket of catalyst to prevent air from reaching the copper chromite. The receiver is repositioned below the dryer, a vacuum drawn, and the ball valve is reopened.

The catalyst is kept out of contact with air until it is transferred to the fluidized bed. Preferably, this is accomplished under a nitrogen or carbon dioxide blanket.

Vacuum in the dryer is kept at 5–10 mm Hg. Virtually all of the vapor is condensed in the first condenser, with very little material collecting in either the entrainment separator or the low temperature condenser.

Analysis of the dry copper chromite collected by this process shows an organic content of about 4%. Analysis of the distillate shows about 8–10% of the alcohol of all chain lengths converted to aldehyde. There is no evidence of high boiling entities such as acetal or hemiacetals. The catalyst level in the distillate is about 0.5%.

EXAMPLE III

In this example, the apparatus cited in Example II is used to process a feed slurry consisting of 25% copper chromite, 44% lauryl alcohol, 15% myristyl alcohol, 7% cetyl alcohol, 8% stearyl alcohol and 1% various other long chain organic compounds.

The vacuum in the dryer is kept at 10–15 mm Hg, (36 kg/hr) and the slurry is pumped to the dryer at a rate of about 80 lb/hr. The feed is preheated to 100° C., and the dryer shell is heated to 240° C. Virtually all of the vapor is condensed in the first condenser, with very little material collecting in either the entrainment separator or the low temperature condenser.

Analysis of the dry copper chromite collected by this process shown an organic content of about 10%. Analysis of the distillate shows about 8–10% of the alcohol of all chain lengths converted to aldehyde. The catalyst level in the distillate is about 0.5%.

EXAMPLE IV

This example describes the use of a 40 cm diameter fluidized bed in regenerating the activity of spent copper chromite catalyst in which the organic residue from ester hydrogenation has been reduced to about 10%. The organic residue is from the hydrogenation of the methyl esters of $C_8$ to $C_{18}$ fatty acids. The fluidized bed apparatus was constructed by Procedyne Corporation of New Brunswick, N.J., in accordance with the teachings of U.S. Pat. No. 4,161,389, Staffin et al., and was equipped with a special screw plate distributor as described in U.S. Pat. No. 4,068,389, Staffin et al. Both patents are incorporated by reference herein. This apparatus acts as a continuous backmixed reactor for the high temperature treatment of spent copper chromite in the presence of molecular oxygen. Copper chromite is fed to the vessel through a sequenced dual valve device, and it exits the bed, via displacement, to a collecting drum.

Gas enters the bottom of the bed through the screw plate distributor, and leaves through the top of the vessel via porous metal filter tubes. Gas is delivered to the vessel by a blower. In this example air acts as the fluidizing and combusting gas, as well as being the major cooling medium for the bed. Additional heat removal is provided by a plate coil cooler located in the center of the bed. The air is preheated initially to raise the bed temperature and initiate the combustion process.

Prior to the commencement of the regeneration process, the bed is filled to a 100 cm depth with "fresh" catalyst, i.e., catalyst that has never been used in the alcohol hydrogenation process. The bed is then heated by the hot fluidizing gas to 315° C., at which point the feeding of spent catalyst is begun. This spent copper chromite catalyst contains about 10% organic material, by weight.

The spent catalyst is fed to the fluidized bed in small increments, at an overall rate of about 20 lb/hr. As each increment enters the vessel, a rapid exothermic reaction occurs. Because of the velocity of the fluidizing gas and the turbulence of the bed, the heat of reaction is quickly and evenly distributed throughout the bed, preventing localized overheating. At this point, the air preheater is turned off, and the temperature of the bed is maintained by balancing the feed rate of spent catalyst, and the velocity of the fluidizing gas.

Catalyst displaced from the reactor vessel by overflow is regenerated copper chromite, and can be reused in the alcohol hydrogenation process.

What is claimed is:

1. A process for regenerating spent copper chromite catalyst which has been used in the hydrogenation of carboxylic acids containing from about 6 to abut 30 carbon atoms or carboxylic acid esters containing from about 7 to about 31 carbon atoms to produce alcohols, the said spent catalyst comprising at least about 50% by weight organic residue from said hydrogenation process, the said regeneration process comprising the steps of:
   (1) subjecting the spent catalyst to a vacuum of from about 1 mm to about 20 mm Hg at a temperature of from about 65° C. to about 320° C. for a time period of less than about one minute to reduce the organic residue content of the spent catalyst to less than about 20% by weight, thereby converting said spent catalyst to a free flowing granular form, and
   (2) heating the vacuum-treated catalyst from Step (1) in an atmosphere comprising molecular oxygen while maintaining the temperature at about 260° C. to about 370° C., whereby any remaining organic residue is burned off and the catalyst is reoxidized.

2. The process of claim 1 wherein the temperature and vacuum pressure in Step (1) are selected such that the time period needed to reduce the organic residue content of the spent catalyst to less than about 25% is less than 30 seconds.

3. The process of claim 2, wherein during transfer of the catalyst from Step (1) to Step (2), the catalyst is kept out of contact with air by blanketing the catalyst with an inert gas or by maintaining a vacuum over the catalyst.

4. The process of claim 2 wherein during transfer of the catalyst from Step (1) to Step (2) the surface of the catalyst is subjected to controlled partial oxidation by slowly contacting the catalyst with air while maintaining the temperature of the catalyst below about 10° C.

5. The process of claims 1, 2, 3 or 4 wherein Step (1) is conducted in a wiped film evaporator.

6. The process of claim 5 wherein in Step (2) the temperature is from about 315° C. to about 370° C.

7. The process of claim 6 wherein the temperature is maintained within the 315° C. to 370° C. range in Step (2) by alternatively contacting the catalyst with oxygen-containing gas and inert gas.

8. The process of claim 6 wherein Step (2) is carried out in a fluidized bed.

9. The process of claim 8 wherein air is used as the oxidizing gas in the fluidized bed.

10. The process of claim 5, wherein the spent catalyst introduced into Step (1) has been used in the process for hydrogenating the methyl esters of $C_6$ to $C_{22}$ carboxylic acids.

11. The process of claim 10 wherein in Step (2) the temperature is from about 315° C. to about 370° C.

12. The process of claim 11 wherein the temperature is maintained within the 315° C. to 370° C. range by alternatively contacting the catalyst with oxygen-containing gas and inert gas.

13. The process of claim 11 wherein Step 2 is carried out in a fluidized bed.

14. The process of claim 13 wherein air is used as the fluidizing and oxidizing gas in the fluidized bed.

* * * * *